United States Patent
Shoshan-Bar-Matz et al.

(10) Patent No.: US 8,034,314 B2
(45) Date of Patent: Oct. 11, 2011

(54) PHOTOREACTIVE COMPOUND SPECIFICALLY BINDING TO CALCIUM BINDING PROTEINS

(75) Inventors: Varda Shoshan-Bar-Matz, Omer (IL); Adrian Israelson, Beer Sheva (IL)

(73) Assignee: The National Institute for Biotechnology in the Negev Ltd., Beer Sheva (IL)

( * ) Notice: Subject to any disclaimer, the term of this patent is extended or adjusted under 35 U.S.C. 154(b) by 1194 days.

(21) Appl. No.: 10/589,170

(22) PCT Filed: Feb. 17, 2005

(86) PCT No.: PCT/IL2005/000203
§ 371 (c)(1), (2), (4) Date: Apr. 3, 2007

(87) PCT Pub. No.: WO2005/079155
PCT Pub. Date: Sep. 1, 2005

(65) Prior Publication Data
US 2007/0298120 A1  Dec. 27, 2007

(30) Foreign Application Priority Data

Feb. 19, 2004  (IL) .......................................... 160492

(51) Int. Cl.
C01B 21/00 (2006.01)
C01B 21/08 (2006.01)
B01D 11/00 (2006.01)
A01N 59/16 (2006.01)
G01N 33/48 (2006.01)
A23J 1/00 (2006.01)
C07K 1/00 (2006.01)

(52) U.S. Cl. .......... 423/410; 423/351; 423/63; 424/617; 436/63; 530/412

(58) Field of Classification Search ........................ None
See application file for complete search history.

(56) References Cited

U.S. PATENT DOCUMENTS

| 4,888,248 A | 12/1989 | Hirai et al. |
| 6,388,001 B1 | 5/2002 | Bergmann et al. |
| 2003/0144570 A1 | 7/2003 | Hunter et al. |

OTHER PUBLICATIONS

Siebald et al.; Preparation and Crystal Structure of Trans-Diazidotetrakis (Trimethylphosphine)Ru(II); Polyhedron vol. 15, No. 23, pp. 4221-4225; 1996.*

Brown et al.; Thermal and Light Induced Decomposition of Azido(bis-2,2'-bipyridine) Complexes of Ruthenium(III); Inorganic Chemistry, vol. 14, No. 8; 1975.*

(Continued)

Primary Examiner — Melvin Mayes
Assistant Examiner — Guinever Gregorio
(74) Attorney, Agent, or Firm — Roach Brown McCarthy & Gruber P.C.; Kevin D. McCarthy (57) ABSTRACT

The present invention provides a photoreactive reagent that binds specifically to $Ca^{2+}$-binding proteins, links to them covalently after photo-activation, and labels them. The novel reagent enables the characterization, purification, inhibition and screening of $Ca^{2+}$-binding proteins, as well as the preparation of a new affinity chromatography matrix and a new protein biosensor. The invention also relates to the use of the reagent in inhibiting apoptosis and necrosis and in diagnosing a disorder associated with a defect in the function of a $Ca^{2+}$-binding protein, and in the preparation of a medicament for treating such disorders.

10 Claims, 11 Drawing Sheets

OTHER PUBLICATIONS

Douglas et al.; Reactions of Coordinated Ligands. II. Azide and Dinitrogen Complexes of Ruthenium; Journal of the American Society; 94:15; 1972.*

Xu Le et al: "Ruthenium red modifies . . . mechanisms" J. Biol. Chem, vol. 274, No. 46, Nov. 12, 1999, pp. 32660-32691, XP002482842.

Kane-Magulre, Leon A.P.et al: "Azidoruthenium (III) Complexes as . . . Complexes" J.Am. Chem. Soc., vol. 92, No. 20, 1970, pp. 5865-5872 (first page now).

Govindaswamy, P et al: "Synthesis, characterization and . . . ligands" J. Organometallic Chem., vol. 689, No. 19, Sep. 22, 2004, pp. 3108-3112, XP004532908.

Israelson, A. et al: "Azido Ruthenium: A New . . . Proteins" Nature Protocols UK, vol. 1, No. 1, Jan. 1, 2006, pp. 111-117, XP001538009.

Israelson, A. et al: "A Photoactivable Probe . . . Proteins" Chem & Biol, Current biol. GB, vol. 12, No. 11, Nov. 1, 2005, pp. 1169-1178, XP005170405.

Leon A.P. et al., "Azidoruthenium (III) complexes as precursors for molecular nitrogen & nitrene complexes" J. Am. Chem. Soc. vol. 92 (20), 1970, pp. 5865-5872.

Zazueta C. et al., "Advances in the Purification . . . " J. Bioenerg. Biomembr. 30 (1998) 489-98.

Vrestal J. et al.: Collection Czechoslov. Chem. Commun. 25 (1960) 2155-60.

Haverstick, D.M. et al.: Cancer Res. 60 (2000) 1002-8.

Hadad N. et al.: J. Biol. Chem. 269 (1994) 26864-9.

Seok W.K. et al.: J.Organomelallic Chem. 559 (1998) 65-71.

Siebald H.G.L. et al.: Polyhedron 15 (1996) 4221-5.

Zazueta C. et al.: J. Bloenerg. Biomembr. 30 (1998) 489-98.

Ying et al.: Biochemistry 30 (1991) 4949-52.

Saito et al: J.Cell Biol. 99 (1984) 875-85.

Gincel D. et al.: Biochem J. 358 (2001) 147-55.

Gincel D. et al.: J. Bioenerget. Biomembr. 32 (2000) 571-83.

J. Biol. Chem. 258 (1983) 11932-6.

Biochem. Biophys. Res. Commun. 104 (2) (1982) 830-6.

Methods in Enzymol. 85 (1982) 241-263.

Lowry O.H. et al: J. Biol. Chem 193 (1951) 265-275.

Shoshan-Barmatz V. & Shaineberg A.: Biochim. Biophys. Acta 1065 (1991) 82-8.

Gregersen H.J. et al.: Adv. Exp. Med. Biol. 269 (1990) 89-91.

* cited by examiner

PHOTOREACTIVE COMPOUND SPECIFICALLY BINDING TO CALCIUM BINDING PROTEINS

FIELD OF THE INVENTION

The present invention relates to a photoreactive reagent that binds specifically to $Ca^{2+}$-binding proteins, links to them covalently after photo-activation, and thus labels them and enables their characterization and purification. The invention also provides methods for the preparation of affinity chromatography matrix and protein biosensors comprising said reagent, and relates to therapeutic and diagnostic uses of said reagent and biosensors.

BACKGROUND OF THE INVENTION

Calcium ($Ca^{2+}$) is a ubiquitous intracellular signal transducer, responsible for controlling numerous cellular processes. It regulates muscle contraction, neurotransmitter release, hormone secretion, cell motility, cell mitosis, and gene expression. $Ca^{2+}$-signaling is employed throughout the life of the organism, beginning with a surge of $Ca^{2+}$ at fertilization and ending with the induction of apoptosis, thereby, at cell death. Calcium is deeply involved in the cell proliferation. Several drugs that block $Ca^{2+}$ entry into the cell, retard the cell growth in human melanoma, lung and colon carcinoma, and prostate cancer [See, e.g., Haverstick, D. M. et al.: Cancer Res. 60 (2000) 1002-8].

There are many proteins involved in the compound role of calcium in the organism having high-affinity or low-affinity $Ca^{2+}$-binding sites. Many of said proteins remain unknown or insufficiently characterized. Despite advances in defining $Ca^{2+}$-dependent activity, considerable experimental difficulties still remain in localizing the protein $Ca^{2+}$-binding sites [Hadad N. et al.: J. Biol. Chem. 269 (1994) 26864-9]. Fundamental to the understanding of normal and abnormal calcium signaling is the knowledge of the proteins involved in this process. It is therefore an object of this invention to provide a compound binding specifically to $Ca^{2+}$-binding proteins.

It is an object of this invention to provide a photoreactive azido-ruthenium (AzRu) based probe which specifically binds to $Ca^{2+}$-binding proteins, and inhibits their activity.

It is another object of this invention to provide an AzRu-based probe which specifically and covalently binds to $Ca^{2+}$-binding sites of $Ca^{2+}$-binding proteins, thereby allowing to localize and to characterize such sites.

It is another object of this invention to provide the use of said AzRu-based compound in producing affinity chromatography matrices binding specifically $Ca^{2+}$-binding proteins, and allowing their purification.

It is still another object of this invention to provide the use of said AzRu-based compound in producing biosensors binding specifically to $Ca^{2+}$-binding proteins, and allowing their characterization.

It is further an object of this invention to provide diagnostic and therapeutic uses of azido-ruthenium compound associated with defects in the function of $Ca^{2+}$-binding proteins.

SUMMARY OF THE INVENTION

This invention provides a new photoreactive azido-ruthenium compound, which exhibits a specific interaction with $Ca^{2+}$-binding proteins. The reagent, azido-ruthenium of this invention (AzRu), was found to specifically inhibit activities of various $Ca^{2+}$-transport mediating proteins, $Ca^{2+}$-regulatory proteins, and $Ca^{2+}$-dependent enzymes. When photo-activated, the reagent binds covalently to the calcium binding site. Azido-ruthenium according to this invention can be synthesized from radiolabeled reagents, which enables to label binding sites in $Ca^{2+}$-binding proteins, and to characterize these important proteins. The compound comprises ruthenium and azide in the molar ratio of 2:1. Said AzRu compound binds covalently after photo-activation by UV irradiation to the $Ca^{2+}$-binding site of said protein. The binding is specific for $Ca^{2+}$-binding proteins. In a preferred embodiment of this invention, the compound contains a radioactive isotope, preferably $^{103}Ru$, and can label radioactively the binding sites in said $Ca^{2+}$-binding proteins. The compound of this invention can bind to $Ca^{2+}$-binding proteins, and inhibit their activity. Among the proteins which can bind the compound of this invention are $Ca^{2+}$-binding proteins selected from proteins involved in signal transduction, muscle contraction, neurotransmitter release, hormone secretion, cell motility, apoptosis, fertilization, cell proliferation, cell mitosis, gene expression: where some of these proteins are associated with mediating $Ca^{2+}$ transport, such as $Ca^{2+}$-pump, the mitochondrial uniporter, channel protein VDAC (voltage dependent anion channel), $Ca^{2+}$ release channel/ryanodine receptor, proteins involved in $Ca^{2+}$ uptake in mitochondria, and the $Ca^{2+}$ pump catalyzing the transport of $Ca^{2+}$ across the sarcoplasmic reticulum membrane. When the compound of this invention is photo-activated after its binding to a protein by UV-irradiation, it binds covalently and thus inhibition of the activity of said protein increases several-fold, compared to the inhibition without photo-activation.

The invention also relates to the method of purifying, identifying, and characterizing $Ca^{2+}$-binding proteins by employing AzRu compound containing ruthenium and azide in molecular ratio of 2:1. When studying function and structure of $Ca^{2+}$-binding proteins, the method of this invention may be combined with methods known in the art, such as SDS-PAGE, autoradiography, MALDI-TOF analysis, LC-MS/MS, protein sequencing, and a sequence homology search. In a preferred embodiment, this invention provides new affinity chromatography technique, comprising binding AzRu to particles of porous polymer that are packed in a column, wherein $Ca^{2+}$-binding proteins are retained in said column, while other proteins pass. Said retained proteins are released by calcium ions. Said particles may comprise agarose, cellulose, or other matrix. Said method of this invention may comprise purifying $Ca^{2+}$-binding proteins, identifying unknown $Ca^{2+}$-binding proteins, inhibiting $Ca^{2+}$-binding proteins, and labeling $Ca^{2+}$-binding proteins. Said labeling may be a radioactive labeling. In a preferred embodiment, the method of this invention comprises the preparation of an affinity resin. In another preferred embodiment, the method according to this invention comprises the preparation of a bio-sensor chip.

The invention provides a process for preparing a photoreactive azido-ruthenium reagent that binds to $Ca^{2+}$-binding proteins, which comprises i) reacting in dark of sodium azide with ruthenium (III) chloride in the presence of HCl, ii) applying the reaction mixture of the previous step onto a chromatographic column, e.g. cation-exchange or hydrophobic interaction column, iii) collecting the fractions containing AzRu, wherein such fractions may be identified, e.g., according to the absorbance at 290 nm, iv) drying the collected fractions, and optionally dissolving said dried fractions and applying them again on a chromatographic column, and drying obtained AzRu reagent. The reagent may eventually be crystallized from methanol. In the process of this invention, HCl has preferably the concentration in the range from 0.5 mol/l to 2 mol/l, and sodium azide and ruthenium chloride react at about 100° C. for about 2 to 4 hrs. This invention further provides a compound of empirical formula $Ru_2N_3Cl_5 \cdot 5H_2O$, and solvates thereof, e.g. solvates further comprising $H_2O$ and HCl.

This invention is also directed to the use of AzRu compound containing ruthenium and azide in a molar ratio of 2:1 in diagnosing disorders associated with $Ca^{2+}$-binding proteins, and in preparing a medicament for treating said disorder. The invention also relates to a pharmaceutical composition containing said AzRu compound, or a solvate thereof, and possibly a carrier, stabilizer, adjuvant, diluent, or excipient. Said AzRu compound, or a composition containing it, may be used in the preparation of a medicament for treating or preventing a disorder associated with a defect in the function of a $Ca^{2+}$-binding protein, wherein said preventing and treating comprise the inhibition of $Ca^{2+}$-binding proteins by said AzRu compound.

BRIEF DESCRIPTION OF THE DRAWINGS

The above and other characteristics and advantages of the invention will be more readily apparent through the following examples, and with reference to the appended drawings, wherein:

FIG. 6. A and B demonstrate the inhibition by AzRu of the $Ca^{2+}$-pump activity in skeletal muscle membranes;

FIG. 7. A to C show the effect of AzRu on calcium uptake and electron transport in isolated mitochondria;

FIG. 10. A and B show the identification of $Ca^{2+}$-binding proteins on SDS-PAGE by using [$^{103}$Ru]AzRu;

FIG. 13. A and B show the protection of U-937 cells against STS-induced apoptotic cell death by AzRu.

DETAILED DESCRIPTION OF THE INVENTION

This invention provides a new azido-ruthenium, which is photoreactive, and exhibits a specific interaction with $Ca^{2+}$-binding proteins. Synthesis of three azido-ruthenium compounds were reported [Seok W. K. et al.: J. Organomelallic Chem. 559 (1998) 65-71; Siebald H. G. L. et al.: Polyhedron 15 (1996) 4221-5; Vrestal J. et al.: Collection Czechoslov. Chem. Commun. 25 (1960) 2155-60]. Effects of these non-photoreactive reagents on biological activities were not described. Another known ruthenium reagents, ruthenium red and Ru360 are not photoreactive. The preferred reagent of this invention can be prepared by reacting sodium azide with ruthenium chloride (III) and purifying the product on a chromatographic column, e.g. cation-exchanger or hydrophobic. Chromatography purification methods, useful for this purpose comprise, for example, CM-cellulose or Sephadex LH-20 columns. IR spectrum of the novel azido-ruthenium (AzRu) product shows the characteristic absorption of the bound azido group at 2072 $cm^{-1}$. It was surprisingly found that the azido-ruthenium compound of this invention interacts with $Ca^{2+}$-binding proteins and inhibits their activity. When photo-activated, by UV-irradiation, the reagent binds covalently to the $Ca^{2+}$-binding sites. The effect of the reagent of this invention on activities of various proteins, including channels, receptors and enzymes, were tested, and it was found by us that the interaction is specific for the $Ca^{2+}$-binding proteins (Table 1). Azido-ruthenium according to this invention can be synthesized from radiolabeled reagents, thus enabling labeling of binding sites in $Ca^{2+}$-binding proteins. Such labeling enables discovering still unknown proteins, explaining still unclear aspects of regulations and signal transduction pathways depending on calcium ions, separating and characterizing the involved peptides and proteins, as well as determining their structure and function.

In one embodiment, to identify $Ca^{2+}$-binding proteins, proteins labeled by radiolabeled reagents are separated by SDS-PAGE, identified by autoradiography, cut from the gel and exposed to cleavage conditions. The degradation products are separated by a second SDS-PAGE, and the Coomassie stained labeled bands are sequenced to identify the $Ca^{2+}$-binding sites. The labeled protein bands can be cut from electrophoresis gels, and subjected to MALDI-TOF analysis or LC-MS/MS, and the identity of the protein can be determined by a sequence homology search.

Above mentioned approach can be used, for example, for identifying mitochondrial systems for transporting $Ca^{2+}$, like ruthenium red-sensitive uniporter, $Na^+$ or $H^+$ dependent efflux mechanisms, and the rapid mode of uptake transporter.

Our results show that azido-ruthenium of this invention specifically inhibits the activity of proteins which mediate $Ca^{2+}$ transport such as the muscle $Ca^{2+}$-pump, the mitochondrial uniporter, and the channel protein VDAC. An AzRu compound according to this invention also inhibits the activity of proteins possessing regulatory $Ca^{2+}$-binding sites such as the muscle $Ca^{2+}$-release channel/ryanodine receptor and calmodulin. In contrast to that, azido-ruthenium has no significant effect on $Ca^{2+}$-independent enzymatic reactions.

Using radioactive AzRu, $Ca^{2+}$-binding proteins can be identified, purified and their functions can be established, e.g., autoradiography helps to localize suspected proteins. In a preferred embodiment, the radioisotope used for the synthesis of AzRu is $^{103}$Ru.

In another preferred embodiment, the AzRu reagent of this invention is used for separation of $Ca^{2+}$-binding proteins by affinity chromatography, wherein the AzRu reagent is covalently attached to an inert support filled in chromatographic column. The support can be, for example, a porous polymer, such as agarose, cellulose, or dextrane, etc. A protein mixture is loaded into the column, $Ca^{2+}$-binding proteins are reversibly retained while other proteins pass. The retained proteins may be released, for example, by a calcium containing buffer.

In another embodiment of this invention, AzRu is coupled to polysaccharides, and is used for construction of unique and novel bio-sensor chips for isolation and identification of $Ca^{2+}$-binding proteins. In a preferred embodiment, this invention enables to identify proteins that have affinity for $Ca^{2+}$-binding proteins, i.e. proteins that are not necessarily calcium binding themselves, but interact with $Ca^{2+}$-binding proteins, forming elements of the signal transduction pathways, often elements that are difficult to detect and identify.

In a preferred embodiment of this invention, surface plasmon resonance (SPR) is used for detecting intermolecular interactions. The chip of this invention can be used, for example, for identifying new $Ca^{2+}$-binding proteins, or sites of interaction; binding affinity and kinetics, as well as epitope map can be also obtained.

Based on the above findings, the present invention is also directed to a pharmaceutical composition for use in inhibiting calcium dependent proteins involved in various disorders associated with $Ca^{2+}$-binding proteins and defects in these proteins.

The invention provides a process for preparing an azido-ruthenium compound, having the ratio $Ru:N_3$ of 2:1, that specifically binds to, and inhibits, $Ca^{2+}$-binding proteins, comprising the steps of:

i) reacting in dark of sodium azide with ruthenium (III) chloride in the presence of HCl, ii) applying the reaction mixture of the previous step onto a chromatographic column, e.g. cation-exchanger or hydrophobic, iii) collecting the fractions which contain the required product, possibly identifying such fractions by measuring absorbance; and optionally iv) steps of drying the collected fractions, redissolving them, rechromatographing them, and drying said compound from methanol, eventually crystallizing it. The process of this invention provides an AzRu product that migrates as a single spot with Rf being about 0.9 during TLC on cellulose F plates, using 0.16 M ammonium formate, pH 8.5 and 20% methanol, said product having an absorbance maximum at about 290 nm, and its absorbance is preferably about from 10,000 to 20,000 at a concentration of 1.0 M in a water solution, usually said absorbance at 290 is about 15,000.

Thus, this invention provides a novel tool to identify, purify and characterize $Ca^{2+}$-binding proteins, and to sequence the $Ca^{2+}$-binding sites. In addition, the requirement for $Ca^{2+}$ in a protein reaction or in the regulation of its activity can be tested. The invention may be useful as a pharmaceutical agent to monitor the involvement of $Ca^{2+}$ in the activity or regulation of proteins. The invention can be used as well for the detection of defected $Ca^{2+}$-binding proteins in certain diseases and disorders.

The invention will be further described and illustrated in the following examples.

EXAMPLES

Materials and General Methods

Chemicals

Aldolase, alkaline phosphatase, ATP, bovine liver catalase, choline oxidase, CM-cellulose, n-decane, glucose 6-phosphate dehydrogenase, glutamate dehydrogenase, glyceraldehyde 3-phosphate dehydrogenase, Hepes, yeast hexokinase, lactate dehydrogenase, leupeptin, luciferase, mannitol, horseradish peroxidase, PMSF, pyruvate kinase, soybean asolectin, sucrose, Tris and Triton X-100 were purchased from Sigma (St. Louis, Mo., USA). [$^{45}$Ca], [$^{103}$Ru] and [$^3$H] ryanodine were purchased from NEN® Life Science Products, Inc. (Boston, USA). Unlabelled ryanodine was obtained from Calbiochem. Sephadex LH-20 was purchased from Amersham Biosciences. n-Octyl-β-D-glucopyranoside (β-OG) was obtained from Bachem AG (Germany). Lauryl-(dimethyl)-amineoxide (LDAO) and ruthenium red (98% pure) were obtained from Fluka (Chemie, GmbH). Ruthenium chloride was purchased from Aldrich. Hydroxyapatite (Bio-Gel HTP) was purchased from Bio-Rad Laboratories (Hercules, Calif.) and Celite from Merck. Synthetic firefly D-luciferin reagent was purchased from Biosynth AG.

Preparations

Ru360 was synthesized according to Ying [Ying et al.: Biochemistry 30 (1991) 4949-52].

Sarcoplasmic reticulum (SR) membranes were prepared from rabbit fast twitch skeletal muscle as described by Saito [Saito et al.: J. Cell Biol. 99 (1984) 875-85]. Mitochondria were isolated from rat liver as described by us previously [Gincel D. et al.: Biochem J. 358 (2001) 147-55]. VDAC was purified by a method developed in our laboratory, using columns of hydroxyapatite and reactive red agarose [Gincel D. et al.: J. Bioenerget. Biomembr. 32 (2000) 571-83].

Calsequestrin was isolated from rabbit skeletal muscle sarcoplasmic reticulum membranes as described by Cala S. E. et al. [J. Biol. Chem. 258 (1983) 11932-6]. Calmodulin was isolated from sheep brain as described by Gopalakrishna R. et al. [Biochem. Biophys. Res. Commun. 104 (2) (1982) 830-6]. Troponin was isolated from rabbit skeletal muscle as described by Potter J. D. [Methods in Enzymol. 85 (1982) 241-65].

Assays

Protein concentrations were determined by the standard Lowry procedure [Lowry O. H. et al: J. Biol. Chem 193 (1951) 224-265]

For the determination of [$^3$H]ryanodine binding, SR membranes were incubated for 20-60 min at 37° C. in a standard binding solution containing 1M NaCl, 20 mM MOPS (pH 7.4), 50 μM free $Ca^{2+}$ and 20 nM [$^3$H]ryanodine. Unbound ryanodine was separated from protein-bound ryanodine by vacuum filtration of the sample through nitrocellulose filters (0.45 μm), followed by two washes with 4 ml ice-cold buffer containing 0.2 M NaCl, 10 mM MOPS (pH 7.4) and 50 μM $CaCl_2$. The retained radioactivity in the dried filters was determined by liquid scintillation counting. Specific binding of [$^3$H]ryanodine was defined as the difference between the binding in the presence of 20 nM [$^3$H]ryanodine and in the presence of 20 μM unlabeled ryanodine.

$Ca^{2+}$-accumulation in freshly prepared mitochondria (0.5 mg/ml) was assayed for 1 to 20 minutes at 30° C. in the presence of 225 mM mannitol, 75 mM sucrose, 120 μM $CaCl_2$ (containing $3 \times 10^4$ cpm/nmol $^{45}Ca^{2+}$), 5 mM HEPES/KOH pH 7.0, and 5 mM succinate with 0.1 mM Pi, or 4 mM $MgCl_2$ with 3 mM ATP. The $Ca^{2+}$-uptake was terminated by rapid Millipore filtration, followed by a wash with 5 ml of 0.15 M KCl. The $Ca^{2+}$-accumulation in SR was determined as described previously [Shoshan-Barmatz V. & Shaineberg A.: Biochim. Biophys. Acta 1065 (1991) 82-8]. Electron transport from succinate to cytochrome c was described in above cited article [Gincel D. et al.: J. Bioenerget. Biomembr. 32 (2000) 571-83].

Reconstitution of purified VDAC into planar lipid bilayer (PLB), single channel current recording, and data analysis were carried out as described in above mentioned publication.

Example 1

Azido-Ruthenium (AzRu) Synthesis

Figure 1:
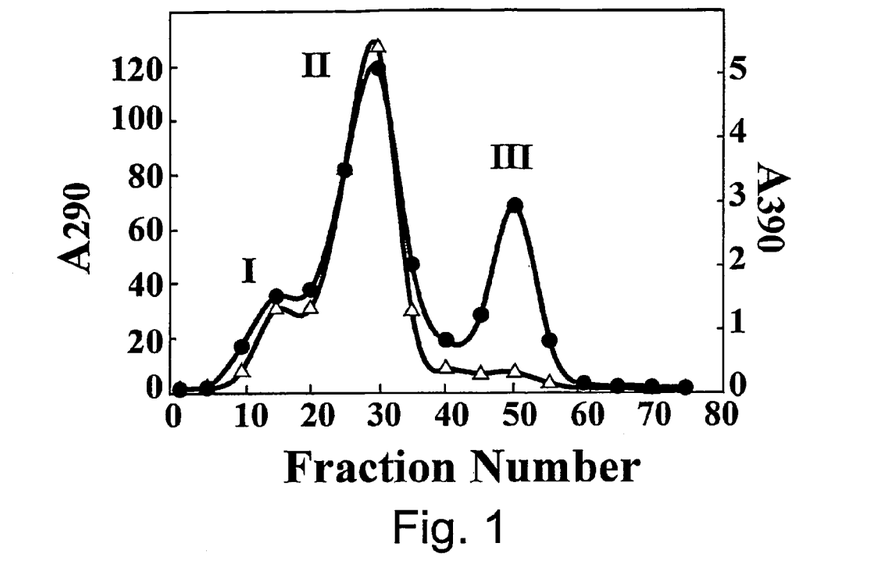
FIG. 1. shows the purification of AzRu on Sephadex LH-20 column.
Figure 2:
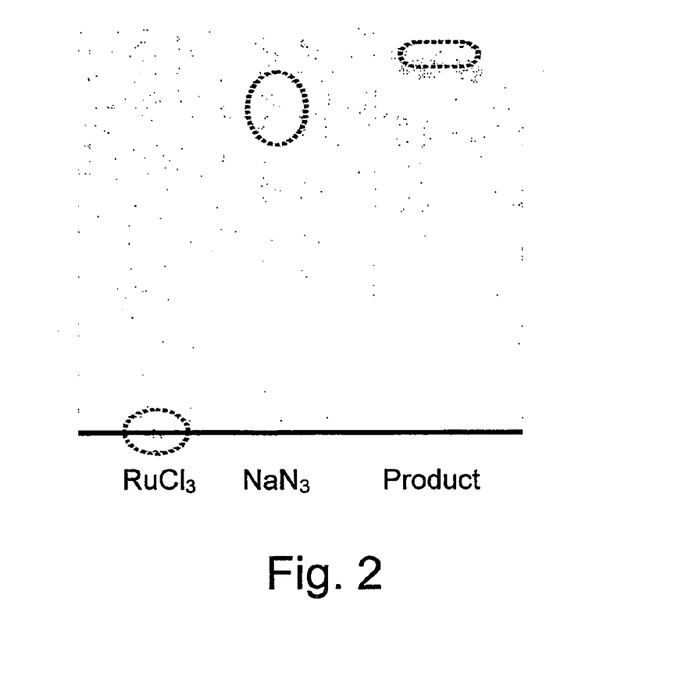
FIG. 2. shows the characterization of AzRu by TLC.
Figure 3:
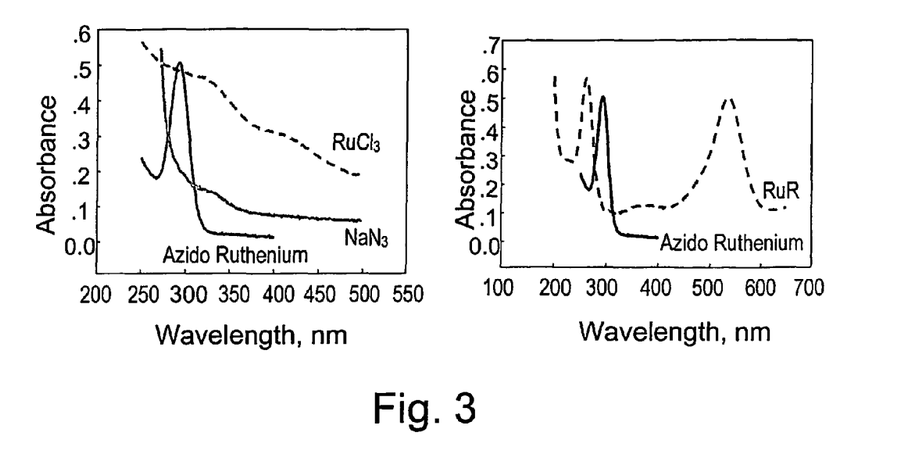
FIG. 3. shows UV spectra of AzRu, ruthenium red, $RuCl_3$, and $NaN_3$.
Figure 4:
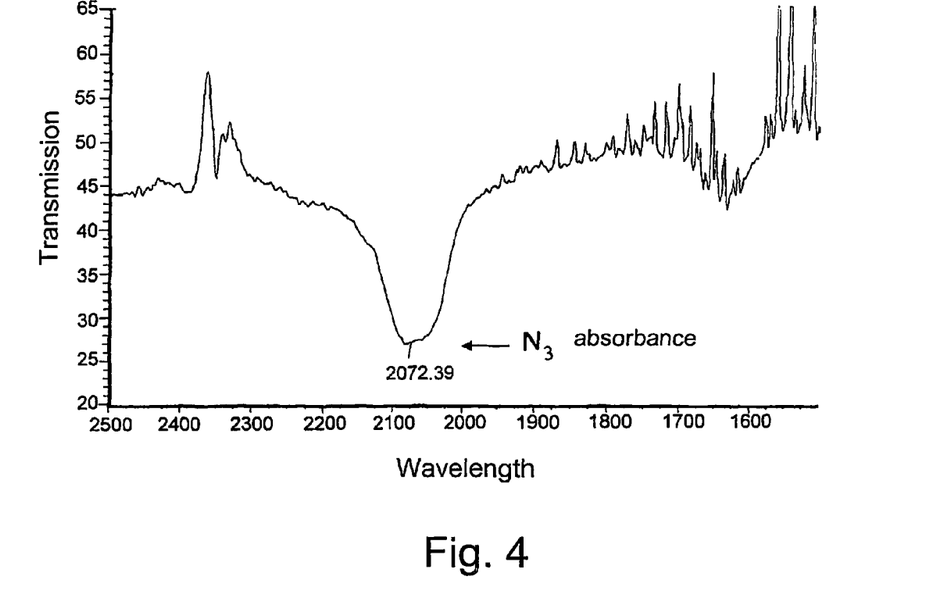
FIG. 4. shows IR spectrum of AzRu.
Figure 5:
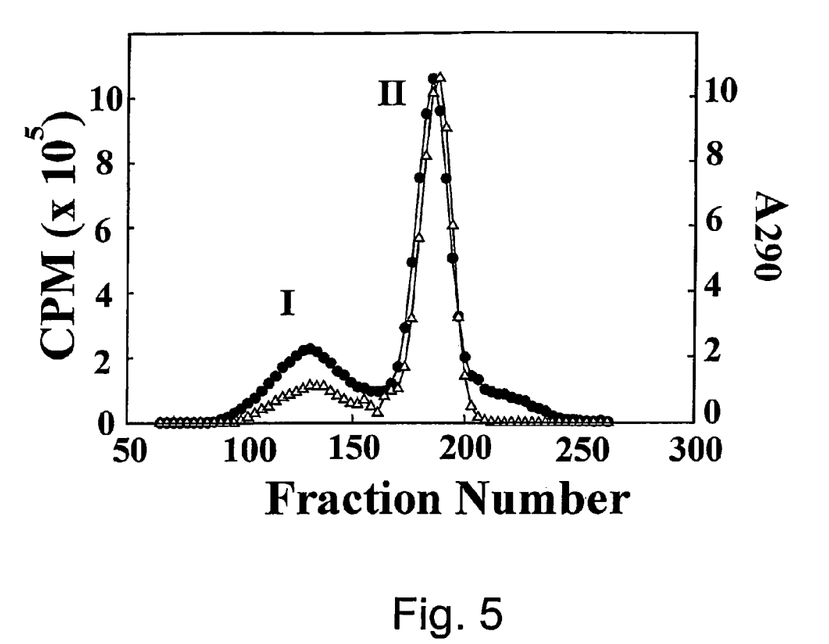
FIG. 5. shows the purification of radioactive AzRu on Sephadex LH-20 column.

All steps were carried out in the dark $RuCl_3$ (29.8 mg, 0.144 mmol) and $NaN_3$ (6.24 mg, 0.096 mmol) were dissolved in 1N HCl (2 ml), silted and incubated at 100° C. for 3 hrs. The sample was then applied to a Sephadex LH-20 column (1.5 cm×44 cm) pre-equilibrated with water (FIG. 1). Free $Ru^{3+}$, but not the product, remained bound to the column matrix. The absorbance at 290 was measured and the peak was collected, lyophilized and analyzed by TLC on cellulose F plates using 0.16 M ammonium formate, pH 8.5 and 20% methanol as a developer. The product migrated as a single spot with Rf=0.9 (FIG. 2). The product is soluble in water, DMF and DMSO, less soluble in methanol, and insoluble in ethanol, ether, chloroform, ethyl acetate, n-butanol, and isopropyl alcohol. The purified product of azido-ruthenium has a maximal absorbance at 290 nm, the absorbance of a solution of 1.0 M being about 15,000. The spectrum of the product is different from that of the substrates and of ruthenium red (RuR), a known inhibitor of calcium dependent activity, which is not photoreactive (FIG. 3). Infrared spectrum of the product indicates the presence of a specific peak representing a bound azido group (FIG. 4). For further purification, the dried product was dissolved in water and subjected to a second chromatography on Sephadex LH-20. The elution of radioactive product [$^{103}$Ru]AzRu is shown in FIG. 5.

Example 2

Purification and Characterization of AzRu

AzRu was prepared as in Example 1, the product eluting as the second peak (FIG. 1), having the absorption maximum at 290 nm, was dried. The elemental analysis of the compound was carried out by SGS Cervac Wolff (France) and the composition was determined in the Department of Chemistry of Ben Gurion University, Israel, to provide the empiric formula of the product: $Ru_2N_3Cl_5 \cdot 5H_2O$ ($H_2O$, HCl).

Example 3

Inhibition of $Ca^{2+}$-Pump Activity

Figure 6A:
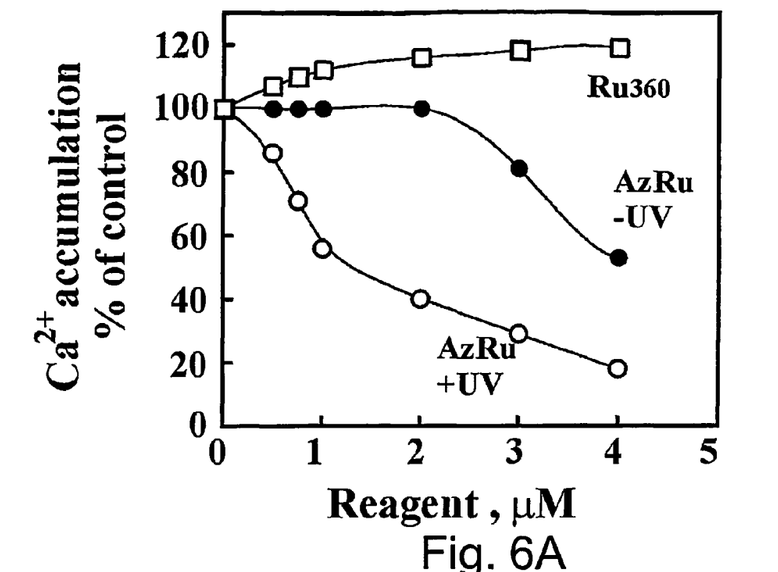
Figure 6B:
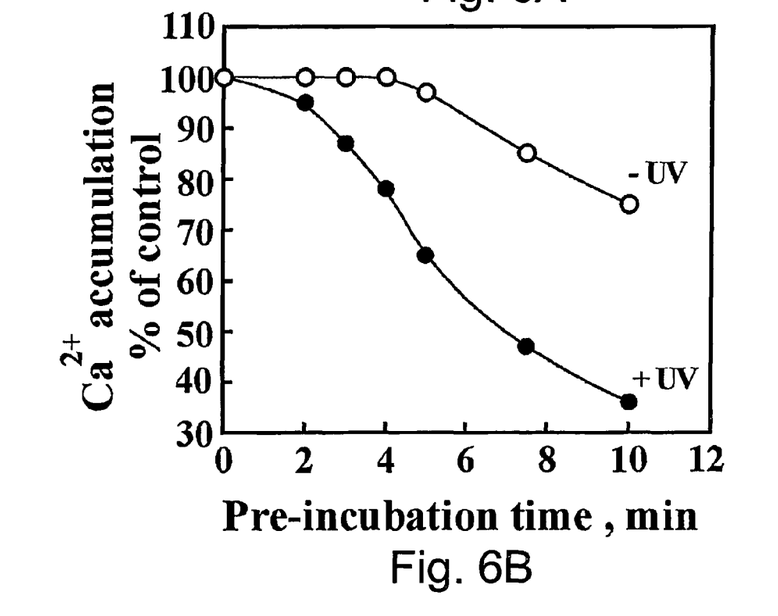

The effect of azido-ruthenium on $Ca^{2+}$-dependent proteins and its photoactivation was demonstrated by the inhibition of the $Ca^{2+}$-pump activity involved in muscle relaxation as shown in FIG. 6. The preparation of SR membranes from skeletal muscle, and the measurement of $Ca^{2+}$-accumulation were carried out as described above. The sensitivity of the $Ca^{2+}$-pump activity to azido-ruthenium was increased more than two-fold by photoactivation, demonstrating that azido-ruthenium of this invention is a photoreactive compound. FIG. 6 shows that the inhibition is dependent on time of UV irradiation, as well as on the concentration of the reagent. UV irradiation increases the inhibitory effect of the compound on $Ca^{2+}$-accumulation by SR membranes, confirming the photoactivation, and suggesting irreversible binding of the reagent to the protein.

Example 4

Specific Inhibition of $Ca^{2+}$ Transport in Mitochondria

Figure 7A:
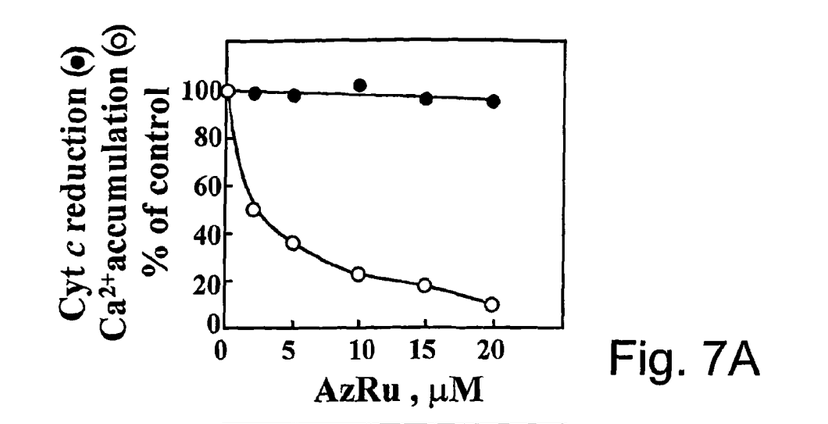
Figure 7B:
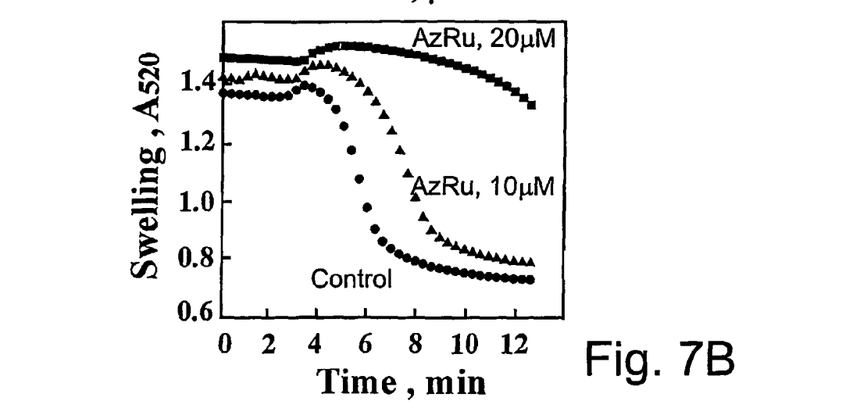
Figure 7C:
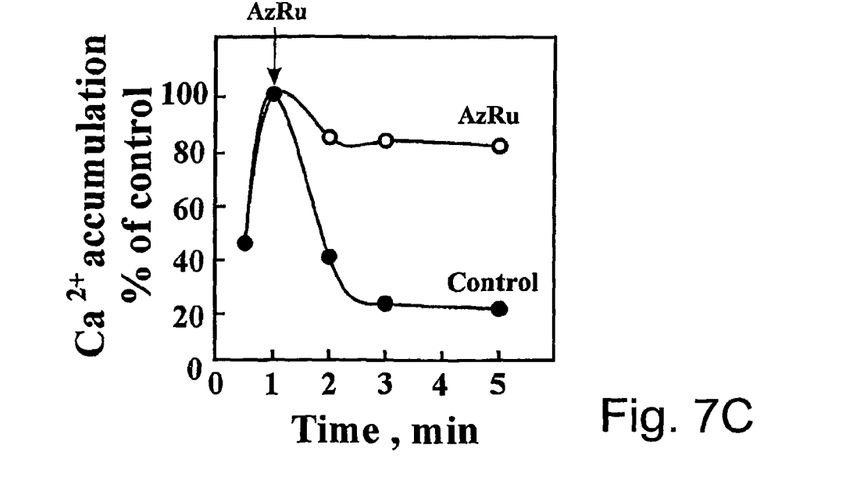

The effect of AzRu on mitochondrial process of electron transport from the donor succinate to the acceptor cytochrome c was characterized as described above. The effect of azido-ruthenium on the $Ca^{2+}$-uptake, and on the electron transport in mitochondria is shown in FIG. 7. Although said electron transfer involves several dozens electron transfer carriers, this reaction was not affected by azido-ruthenium of this invention. On the other hand, $Ca^{2+}$ transport, which is carried out by a yet unidentified uniporter protein, was inhibited by azido-ruthenium, demonstrating the specificity of azido-ruthenium of this invention.

Example 5

Inhibition of Ryanodine Binding to SR Membranes by AzRu

Figure 8:
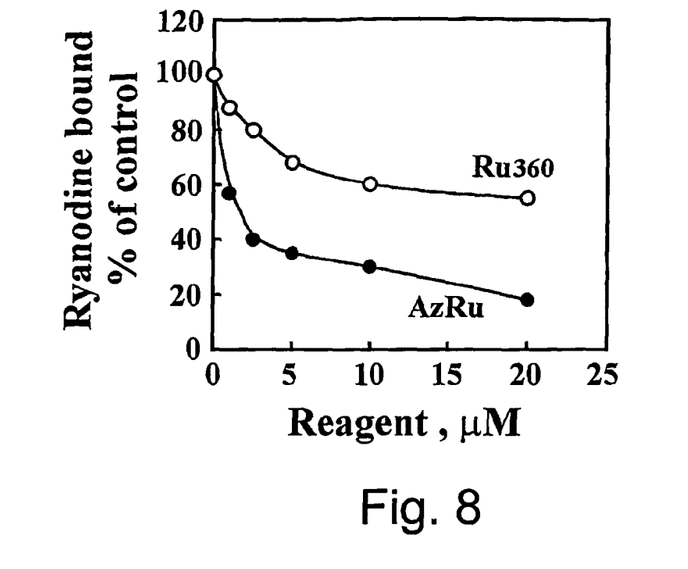
FIG. 8. shows the inhibition of ryanodine binding to its receptor by AzRu.
Figure 9:
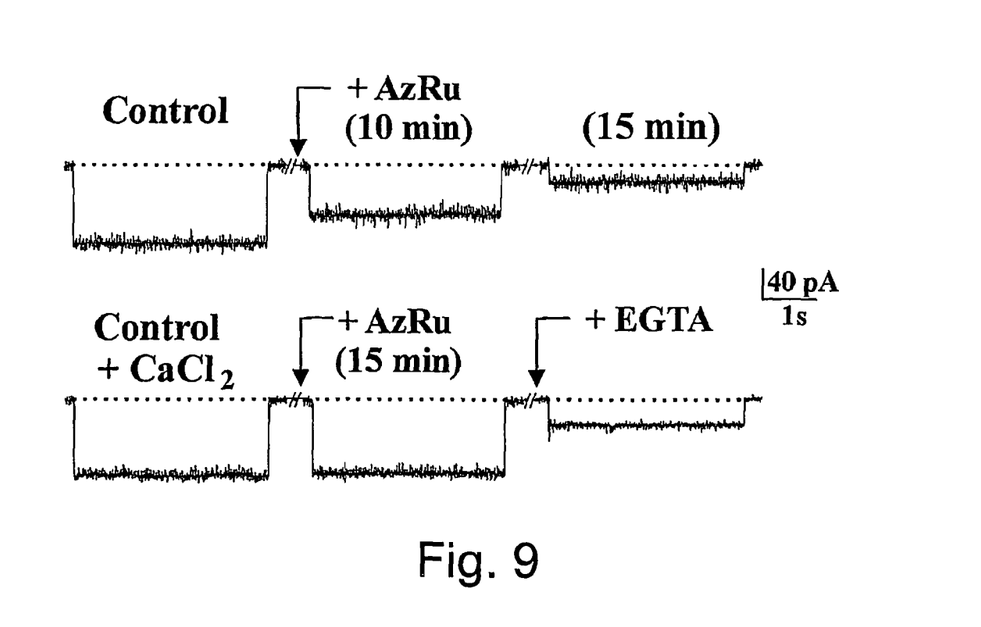
FIG. 9. shows the inhibition of VDAC channel activity by AzRu.

The effect of azido-ruthenium on the binding of the toxic alkaloid ryanodine to its receptor, known as the $Ca^{2+}$-release channel that possesses regulatory $Ca^{2+}$-binding sites, was measured as described above. Azido-ruthenium of this invention strongly inhibited the binding of ryanodine to SR membranes, as demonstrated in FIG. 8, in which a comparison is also shown with Ru360.

Example 6

VDAC Channel Closure

VDAC is a channel protein which transports $Ca^{2+}$ across the mitochondrial outer membrane. It possesses $Ca^{2+}$-binding sites [Gincel D. et al.: Biochem J. 358 (2001) 147-55] and thus is involved in regulation of its own activity. Azido-ruthenium inhibited the channel activity of VDAC. Purified VDAC was reconstituted into a planar lipid bilayer as multichannels. The channel activity was measured as the ions passed the current across the bilayer in response to a voltage gradient of 10 mV, as a function of time. In the absence of AzRu, VDAC is stable in a long-lived, fully opened state and remains open for up to 2 hours of recording. However, addition of AzRu to the same channel induced VDAC closure, in a time-dependent manner. $Ca^{2+}$, in the presence of 1 M NaCl, prevented the inhibitory effect of AzRu on VDAC activity. As has been shown for RuR [Gincel D. et al.: Biochem J. 358 (2001) 147-55], chelation of $Ca^{2+}$ with EGTA re-established AzRu inhibition, suggesting specific interaction of AzRu with VDAC $Ca^{2+}$-binding sites. AzRu also decreased VDAC conductance in multi-channel experiments at all voltages tested and stabilized VDAC conductance at a constant low level regardless of the voltage gradient applied. Similar results have been obtained with RuR and Ru360.

Example 7

Specific Inhibition of $Ca^{2+}$-Dependent Reactions by AzRu

The specificity of the binding of AzRu to $Ca^{2+}$-binding proteins is demonstrated by testing its effects on the activity of different enzymes. The results, summarized in Table 1, indicate that the activities of $Ca^{2+}$-independent proteins such as glutamate dehydrogenase, lactate dehydrogenase, glyceraldehyde 3-phosphate dehydrogenase, glucose 6-phosphate dehydrogenase, choline oxidase, catalase, lysozyme, aldolase, alkaline phosphatase, as well as electron transfer in mitochondria involving over two dozen polypeptides, were only slightly inhibited by the reagent (less than 10% at 100 μM). In contrast, the activities of $Ca^{2+}$-dependent proteins were strongly inhibited by azido-ruthenium (up to 90% at ≦20 μM). The inhibition was observed for various proteins with different activities. Such proteins include, for example, proteins which catalyze the transport of $Ca^{2+}$ across the membrane by distinct mechanisms, all of which involve $Ca^{2+}$-binding to the protein, like the $Ca^{2+}$-pump that transports $Ca^{2+}$ at the expense of ATP hydrolysis, and the uniporter protein which transports $Ca^{2+}$ accumulated in the mitochondrial matrix as a result of the membrane potential established by the electron transport chain. Another inhibited activity is that of the ryanodine receptor, $Ca^{2+}$-release channel, which possesses regulatory $Ca^{2+}$-binding sites that control its channel activity and its ability to bind the toxic alkaloid ryanodine. The results also indicate that the activities of $Mg^{2+}$-dependent proteins, such as yeast and brain hexokinase, pyruvate kinase, luciferase and ($Na^+/K^+$)ATPase, and the $Zn^{2+}$-sensitive KCNK0 channel were not affected or were weakly inhibited at high AzRu concentrations (~30% at 100 μM).

TABLE 1

Effect of AzRu on $Ca^{2++}$- or $Mg^{2++}$-dependent or -independent or $Zn^{2+}$-sensitive proteins, as described in Example 7. Protein activity was assayed in the absence and the presence of different concentrations of AzRu, and the degree of inhibition by 20 or 100 μM of AzRu is presented. The results are the mean ± SEM of 3 to 6 experiments.

| Activity assayed | AzRu (20 μM) | AzRu (100 μM) | Divalent cation involved |
|---|---|---|---|
| 1. $Ca^{2+}$ uptake in SR (SERCA) | 13 ± 6 | | $Ca^{2+}$ |
| 2. $Ca^{2+}$ uptake in mitochondria | 11 ± 4 | | |
| 3. Ryanodine binding by SRRyR | 18 ± 6 | | |
| 4. VDAC conductance | 19 ± 5 | | |
| 5. Peroxidase | 39 ± 4 | | |
| 6. CaMKII-dependent GAPDH | 6 ± 2 | | |
| 7. $Ca^{2+}$-dependent mitochondrial swelling(a) | 0 | | |
| 8. Yeast hexokinase | 77 ± 5 | 64 ± 4 | $Mg^{2+}$ |

TABLE 1-continued

Effect of AzRu on $Ca^{2++}$ or $Mg^{2++}$ dependent or -independent or $Zn^{2+}$ sensitive proteins, as described in Example 7. Protein activity was assayed in the absence and the presence of different concentrations of AzRu, and the degree of inhibition by 20 or 100 μM of AzRu is presented. The results are the mean ± SEM of 3 to 6 experiments.

| Activity assayed | Activity (% of control) | | Divalent cation involved |
|---|---|---|---|
| | AzRu (20 μM) | AzRu (100 μM) | |
| 9. Brain hexokinase | 73 ± 7 | 61 ± 3 | |
| 10. Pyruvate kinase | 97 ± 7 | 81 ± 6 | |
| 11. Luciferase | 97 ± 1 | 67 ± 3 | |
| 12. ($Na^+/K^+$)ATPase | 92 ± 5 | 71 ± 4 | |
| 13. $K^+$ channel (KCKN0) | 100 ± 0.3 | | $Zn^{2+}$ |
| 14. Glutamate dehydrogenase[b] | | 101 ± 5 | None |
| 15. Lactate dehydrogenase | | 91 ± 4 | |
| 16. G-6-P dehydrogenase | | 101 ± 7 | |
| 17. GAP dehydrogenase | | 102 ± 5 | |
| 18. Alkaline phosphatase | | 86 ± 5 | |
| 19. Succinate-cytochrome c oxido-reductase | | 95 ± 5 | |
| 20. Lysozyme | | 101 ± 3 | |
| 21. Aldolase | | 78 ± 7 | |
| 22. Catalase | | 118 ± 8 | |
| 23. Choline oxidase | | 85 ± 3 | |

[a]PTP opening was completely inhibited at this concentration of AzRu.
[b]The enzyme possesses $Ca^{2+}$-binding site(s) that are not involved in its activity.

Example 8

Identification of Unknown $Ca^{2+}$-Binding Proteins

Figure 10A:
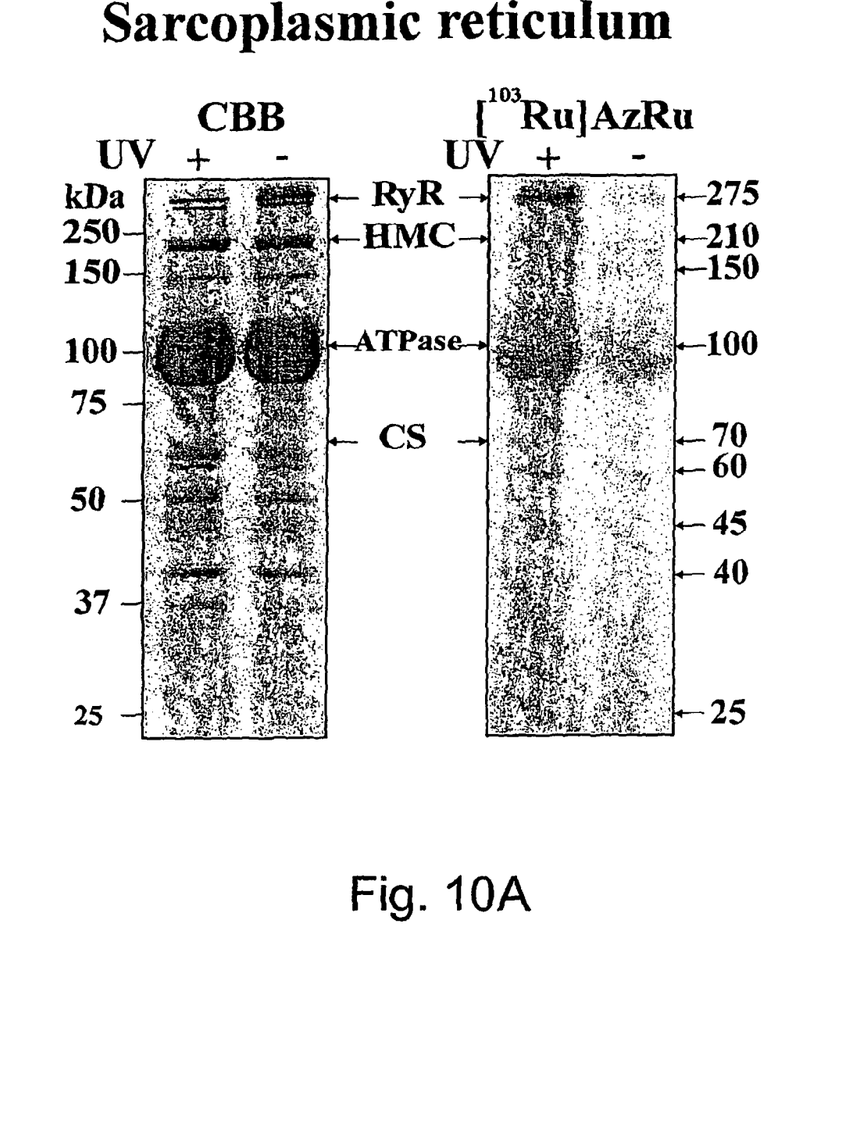
Figure 10B:
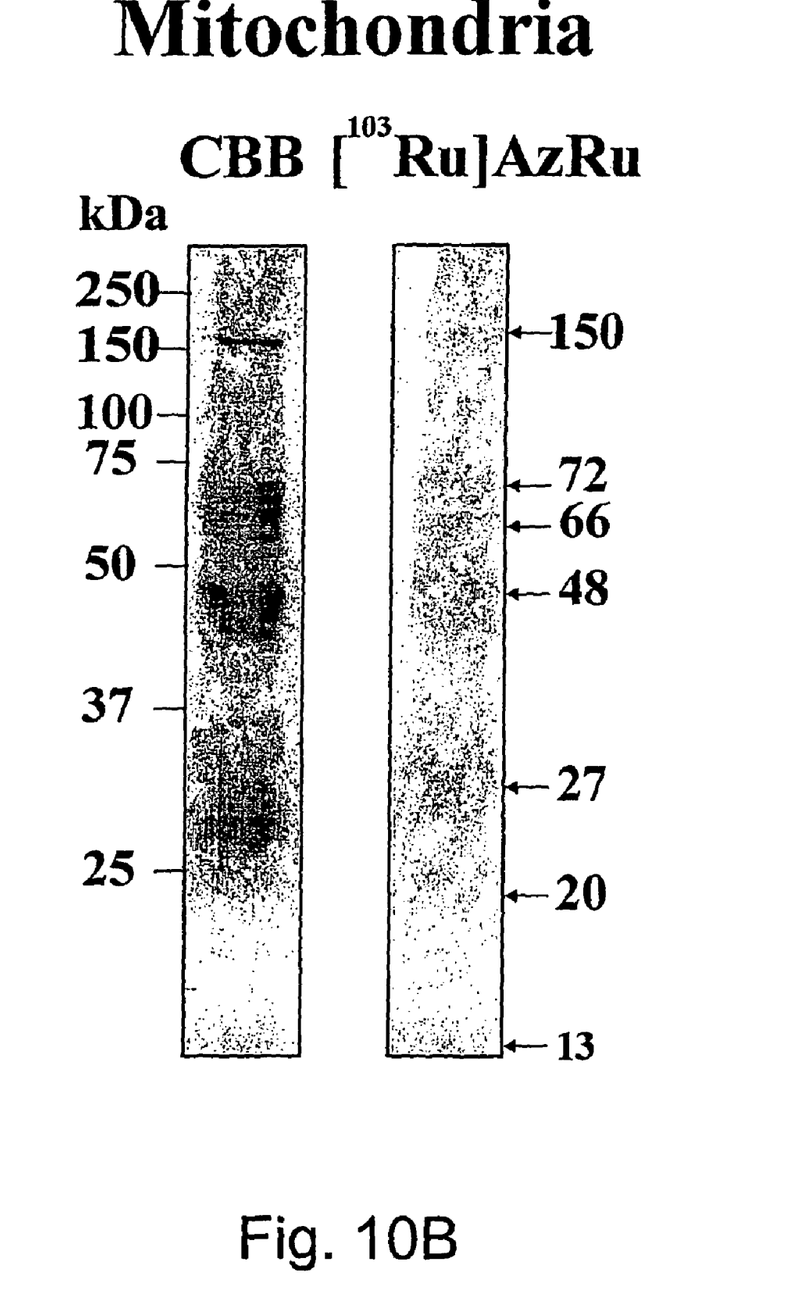

By using radiolabeled [$^{103}$Ru]azido-ruthenium, it is possible to identify $Ca^{2+}$-binding proteins in a biological sample such as whole cells, isolated mitochondria, ER, or other protein containing fractions. UV irradiation of SR or mitochondria in the presence of [$^{103}$Ru]AzRu resulted in its covalent binding to several proteins, as revealed by SDS-PAGE followed by Coomassie staining and autoradiography. As expected for the photoreactive [$^{103}$Ru]AzRu, the labeling of the proteins was significantly increased upon UV irradiation, indicating the formation of a stable covalent bond. In skeletal muscle SR incubated with 0.5 nmol [$^{103}$Ru]AzRu/mg protein (0.5 μM) with or without UV irradiation, nine out of about thirty proteins stained by Coomassie were labeled with [$^{103}$Ru]AzRu. Among the labeled proteins are known $Ca^{2+}$-binding proteins such as RyR, myosin, $Ca^{2+}$-ATPase and calsequestrin, but there were also two unidentified proteins of 37 and 25 kDa (FIG. 10 A). Similarly, in an isolated mitochondrial membranal fraction from which soluble proteins were extracted, photoactivated [$^{103}$Ru]AzRu labeled seven out of about twenty seven proteins stained by Coomassie (FIG. 10 B). Weak [$^{103}$Ru]AzRu labeling of the proteins was observed with no UV irradiation indicating a very stable interaction, which is not surprising when considering the reported labeling of mitochondrial proteins with the non-photoreactive reagent [$^{103}$Ru]Ru360 [Zazueta C. et al.: J. Bioenerg. Biomembr. 30 (1998) 489-98].

Example 9

Affinity Chromatography (Afch)

Figure 11:
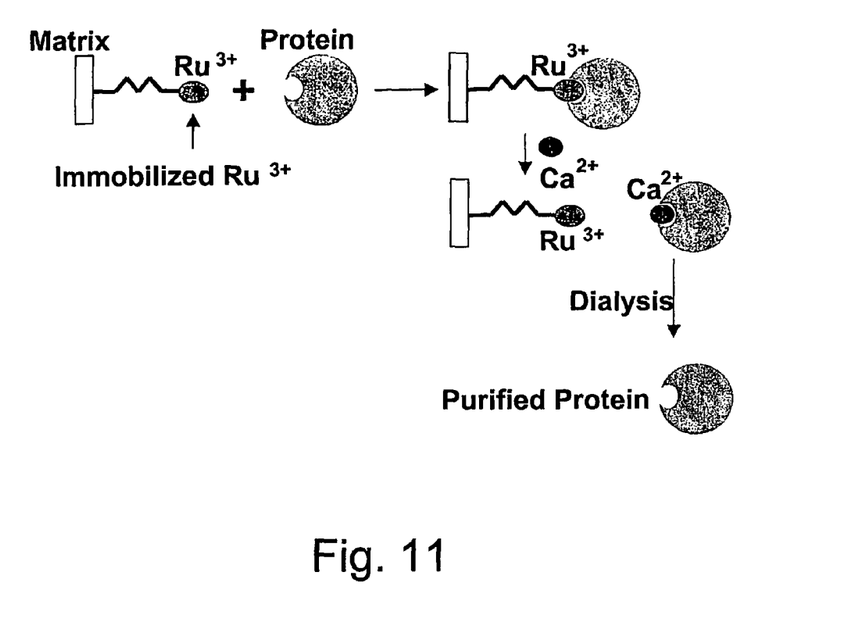
FIG. 11. illustrates the use of AzRu in affinity chromatography.

The specific reversible interaction between a $Ca^{2+}$-binding protein and azido-ruthenium can be exploited in separation of $Ca^{2+}$-binding proteins by affinity chromatography (FIG. 11). Azido-ruthenium of this invention can be coupled to an inert support such as agarose, polyacrylamide or polystyrene by photoactivation, for example cellulose or Sepharose[R] beads can be used for said covalent attachment. From the proteins applied to the column, only $Ca^{2+}$-binding proteins interact with the ruthenium bound in the column, and are retained. The retained proteins can be eluted with a $Ca^{2+}$-containing buffer. Proteins eluted with $Ca^{2+}$ represent $Ca^{2+}$-binding proteins. The proteins can be sequenced and the sequences can be used for the sequence homology search and identification of the proteins.

Example 10

Purification of $Ca^{2+}$-Binding Proteins Using Afch on AzRu Column

AzRu, 4.5 mg, obtained as described in Examples 1 and 2, was incubated with cellulose fibers (Sigma-Aldrich), 1.25 g, in the presence of 10 mM carbonate buffer, pH 7.5, irradiated by UV light for 7 times 2 minutes with short intervals between, and left overnight. The unbound AzRu was removed by washing with said buffer to provide AzRu-cellulose. The protein preparations were applied to the column, and, after washing with said buffer, eluted from the column with said buffer further containing 2-20 mM $CaCl_2$.

Figure 12:
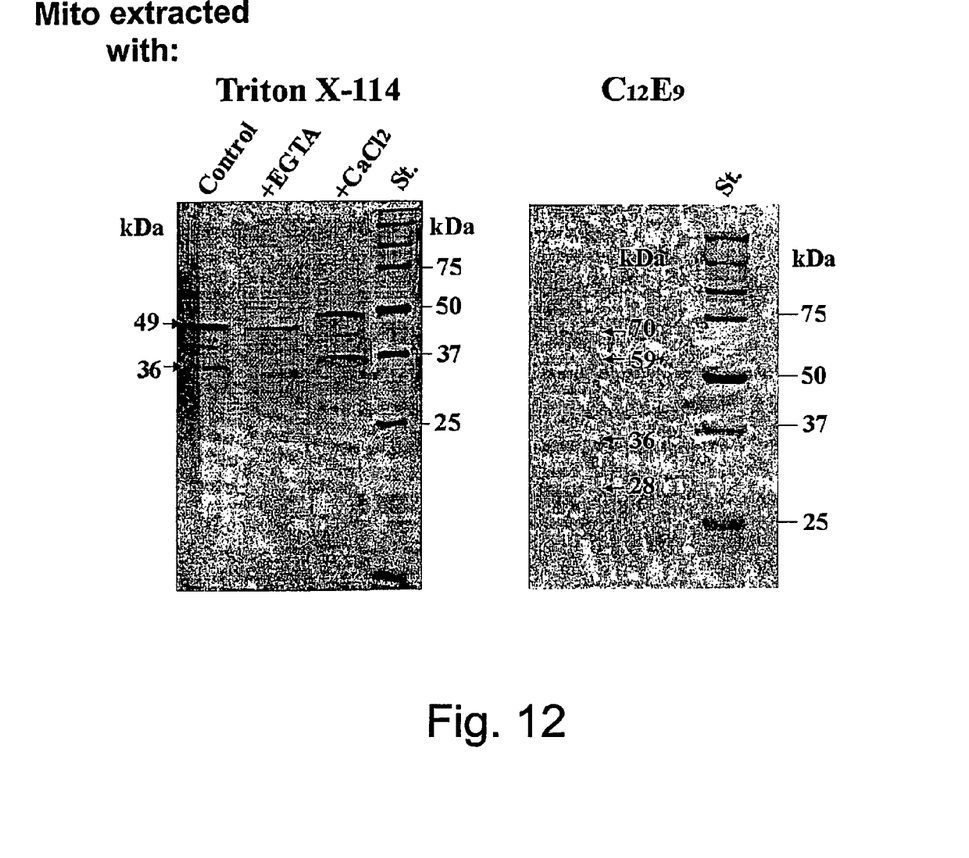
FIG. 12. shows SDS-PAGE of $Ca^{2+}$-binding proteins isolated by AzRu-affinity chromatography.

Rat liver mitochondria, rabbit sarcoplasmic reticulum, rat brain extract, calsequestrin, calmodulin, and troponin were isolated as described above. In order to solubilize the rat liver mitochondrial membrane proteins, mitochondria were treated with 3% Triton X-100, 2% $C_{12}E_9$ or 3% Triton X-114. To some of the eluted proteins, either EGTA (2 mM) or $CaCl_2$ (2 mM) was added, and the samples were subjected to SDS-PAGE (FIG. 12). It can be seen that $CaCl_2$ shifts the electrophoretic mobility of the proteins, which was demonstrated for some known $Ca^{2+}$-binding proteins [Gregersen H. J. et al.: Adv. Exp. Med. Biol. 269 (1990) 89-92].

Among several dozens of proteins applied to the column, only few proteins were bound to the column and were eluted with $CaCl_2$. Some of the proteins that were eluted from the column with the $CaCl_2$-containing buffer were identified by MALDI-TOF analysis and are presented in Table 2. The results clearly indicate the specificity of the AzRu-cellulose column to $Ca^{2+}$-binding proteins.

TABLE 2

Proteins eluted by affinity chromatography on AzRu column according to Example 10

| Preparation applied | Protein MW (kDa) | Identification by MALDI TOF/LC/MS | Metal binding |
|---|---|---|---|
| Rat liver mitochondria | 69 | Albumin precursor | + |
| | 33 | Malate dehydrogenase | + |
| | 45 | Aspartate aminotransferase | + |
| | 28 | Unknown | + |
| | 36 | Unknown | + |
| Rabbit skeletal muscle sarcoplasmic reticulum | 26 | Triosephosphate isomerase | + |
| | 49 | Enolase | + |
| | 58 | Unknown | + |
| Purified protein | Calsequestrin | | + |
| | Calmodulin | | + |
| | Troponin | | + |
| Rat brain extract | Calbindin | | + |

Example 11

Development of Novel AzRu-Based Bio-Sensor Chips

The specific interaction of AzRu with $Ca^{2+}$-binding proteins enables to develop a biosensor chip for real-time monitoring of macromolecular interactions with $Ca^{2+}$. It can be an optical biosensor using surface plasmon resonance (SPR). In principle, the SPR-based technique detects mass and has been designed for the study of biomolecular binding and therefore provides an invaluable tool for proteomics studies of the relationship between protein structure and function. The AzRu-based bio-sensor chip is an optical biosensor that contains AzRu interacting specifically with $Ca^{2+}$-binding proteins. Some of the potential applications include:

i) Identification of new $Ca^{2+}$-binding proteins. By applying protein containing sample to the chip; only $Ca^{2+}$-binding proteins would interact with the reagent bound to the chip. Those proteins could be eluted with a $Ca^{2+}$-containing buffer. Identification of the eluted proteins can be done by the techniques known in the art, such as MALDI-TOF, LC-MS/MS, interactions with antibodies, etc. The chip requires small amounts of the protein relative to column, and a $Ca^{2+}$-eluted protein can be obtained within 10 min.

ii) The second chip type allows identification of proteins interacting with $Ca^{2+}$-binding proteins. Proteins often function as a part of multi-protein compounds; identifying the individual proteins and determining their sites of interaction within the compound are essential for defining their mode of action and function. Chips containing known $Ca^{2+}$-binding proteins can be used for the identification of other proteins specifically interacting with them.

One of the challenges, facing life sciences researchers today, is bridging the gap between the knowledge of genomic sequence and its protein products at one side, and the understanding of the protein function and cellular behavior at the other side. This invention can contribute to said bridging. A novel chip containing several dozens of known $Ca^{2+}$-binding proteins can be used in searching for their interacting partners. Binding affinity and kinetics, binding stoichiometry, binding specificity, and epitope mapping can be obtained by charging the chip with known $Ca^{2+}$-binding proteins and studying their interaction with known proteins. Alternatively, the protein-charged chip can be used to search for unknown interacting protein. In this case the chip will be exposed to potential protein candidates. To identify the interacting protein, the chip will be exposed to $Ca^{2+}$ or EGTA to dissociate said interacting protein from the chip, and the protein will be subjected to analysis by known methods, such as MALDI-TOF, LC-MS/MS, etc. The invention, in one of its aspects, can provide a tool for fast screening of proteins, for example proteins that are involved in cross-talk within the cell or proteins modified in certain pathological conditions, thus adding another general technique to those provided by genomics and proteomics.

Example 12

AzRu Inhibition of Apoptotic and Necrotic Cell Death

Cellular $Ca^{2+}$ signals are crucial in the control of most physiological processes including cell injury and programmed cell death (apoptosis). This regulation is mediated through $Ca^{2+}$ interaction with a number of $Ca^{2+}$-dependent enzymes such as phospholipases, proteases, and nucleases. Mitochondria and ER play pivotal roles in regulating intracellular $Ca^{2+}$ content and thereby involved in apoptotic cell death. Moreover, members of the Bcl-2 family, a group of proteins that plays important roles in apoptosis regulation, appear to differentially regulate intracellular $Ca^{2+}$ level.

The U-937 human monocytic cell line was grown under an atmosphere of 95% air and 5% $CO_2$ in RPMI 1640 supplemented with 10% fetal calf serum (FCS), 1 mM L-glutamine, 100 U/ml penicillin, and 100 µg/ml streptomycin. Cells were plated at a density of $5.4 \times 10^4$ cells/cm² in 24-well plates and then incubated with or without AzRu for 18 hr before exposure to 1.25 µM staurosporine (STS) to induce apoptosis. Cell viability was analyzed 5 and 7 hrs after STS addition by staining with 100 µg/ml acridine orange (AcOr) and 100 µg/ml ethidium bromide (EtBr) in PBS. The cells were then visualized by fluorescence microscopy (Olympus IX51) and images were recorded on an Olympus DP70 camera, using an SWB filter.

Figure 13A:
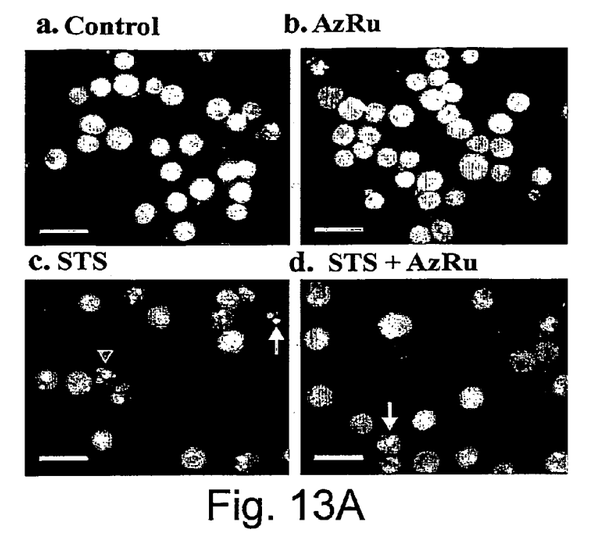
Figure 13B:
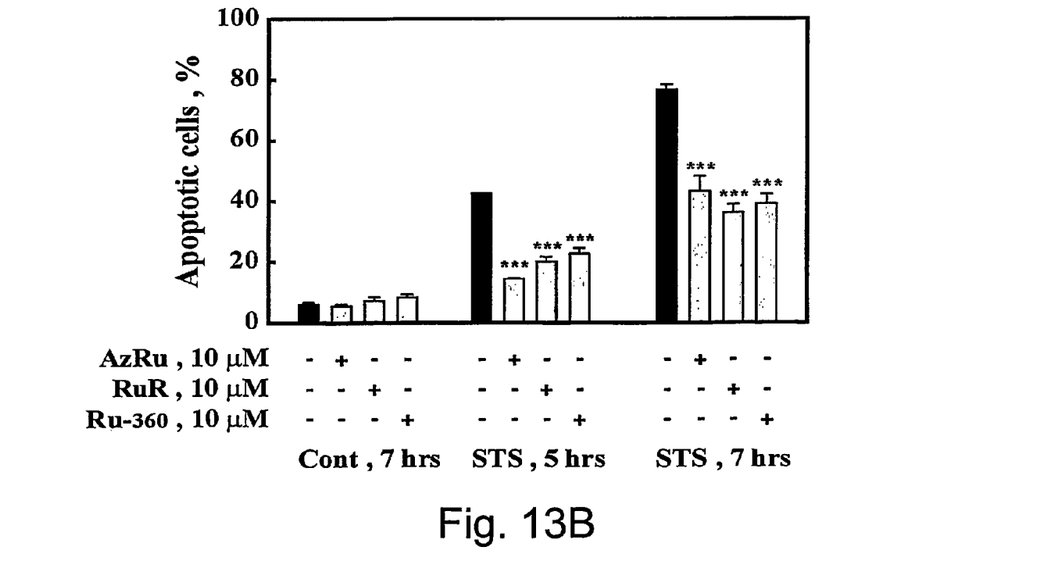

The effect of AzRu on apoptotic cell death induced by exposure of U-937 cells to STS is shown in FIG. 13. Exposure of the cells to STS for 5 or 7 hrs resulted in apoptotic cell death of about 42% and 76% of the cells, respectively, whereas only 6% of the STS non-exposed cells died. AzRu, added 18 h before exposure to STS, dramatically reduced STS-activated apoptotic cell death by about 75% and 47% after 5 and 7 h of exposure to STS, respectively. AzRu had no effect on the viability of the cells that were not exposed to STS. In FIG. 13 A, U-937 cells were incubated without (a, c) or with AzRu (10 µM) (b,d) for 18 hrs and thereafter were exposed to STS (1.25 µM) (c and d). After five hours the cells were stained with acridine orange and ethidium bromide. Arrows indicate cells in early apoptotic state, represented as degraded nucleus, but with intact cell membrane (stained by acridine orange). Arrowheads indicate a late apoptotic state, as shown by the presence of a degraded nucleus (stained by both acridine orange and ethidium bromide). Scale bar, 20 µm. In FIG. 13 B, quantitative analysis of apoptotic cell death in control cells and cells exposed to AzRu was assessed 5 and 7 hr after their exposure to STS (1.25 by ANOVA and t-test. P<0.001 was considered statistically significant (***). Data are the means±SEM, n=3. In each independent experiment, approximately 200 cells were counted for each treatment.

Example 13

Comparison of RuR, Ru360 and AzRu Effects

The hexavalent RuR and the trivalent Ru360 have been employed in various studies as inhibitors of $Ca^{2+}$-dependent reactions. As shown here, even with no photoactivation, AzRu, in contrast to RuR and Ru360, was effective in inhibiting the SR $Ca^{2+}$-pump (Table 3). AzRu was also more effective than RuR or Ru360, with or without photoactivation, in inhibiting the $Ca^{2+}$-dependent binding of ryanodine to RyR (Table 3). This may open the way to inhibit other $Ca^{2+}$-dependent activities that are not sensitive to RuR, such as the plasma membrane $Ca^{2+}$-ATPase. In intact cells, RuR was shown to slowly cross the plasma membrane and to protect against cell death induced by various stimuli. AzRu protected against apoptotic cell death induced by STS (FIG. 13), suggesting that AzRu is able to enter into the cell. RuR was employed to improve mitochondrial production in ischemic reperfused pig myocardium, was employed in the nervous system to follow neuronal death progress and can act as an anti-oxidant in certain conditions. Considering the potent activity of AzRu in RuR-insensitive reactions (see Table 3), its applications in various biological studies should be explored. $Ca^{2+}$ accumulation in SR and mitochondria was assayed as described above in the absence and presence of different concentrations of RuR (0.05-100 µM), Ru360 (0.01-100 µM) or AzRu (0.1-100 µM). The concentration required for 50% inhibition ($IC_{50}$) was derived from the plot of $Ca^{2+}$ accumulation activity or ryanodine binding as a function of the reagent concentration. The results are the mean±SEM of 3 to 5 experiments (Table 3).

TABLE 3

Comparison of RuR, Ru360 and AzRu sensitivity of different $Ca^{2+}$-dependent activities.

| Assay | $IC_{50}$, μM | | | |
|---|---|---|---|---|
| | RuR | Ru360 | AzRu | AzRu (+UV) |
| $Ca^{2+}$ accumulation in SR | a | a | 4.91 ± 0.055 | 1.01 ± 0.095 |
| $Ca^{2+}$ accumulation in mitochondria | 0.16 ± 0.03 | 0.067 ± 0.008 | 1.78 ± 0.12 | b |
| Ryanodine binding in SR | 7.2 ± 0.55 | 14.8 ± 2.8 | 2.9 ± 0.17 | 1.21 ± 0.06 | a—No inhibition, but rather stimulation was obtained.
b—Data not presented because UV irradiation of mitochondria resulted in partial inhibition of electron transport, and thereby inhibition of the membrane potential-supported $Ca^{2+}$ accumulation.

While this invention has been described in terms of some specific example, modifications and variations are possible. It is therefore understood that within the scope of the appended claims, the invention may be realized otherwise than as specifically described.

The invention claimed is:

1. A method for inhibiting the calcium-binding activity of a $Ca^{2+}$-binding protein, comprising
    i) providing a photoreactive azido-ruthenium (AzRu) compound which contains in its molecule ruthenium, azido group, and chlorine in the molar ratio of 2:1:5;
    ii) contacting said AzRu compound with said $Ca^{2+}$-binding protein in order to inhibit the calcium-binding activity of said $Ca^{2+}$-binding protein; and optionally
    iii) applying UV irradiation for covalently binding said AzRu compound to said $Ca^{2+}$-binding protein.

2. A method according to claim 1, wherein said compound comprises bound water molecules.

3. A method according to claim 1, wherein one atom in said compound is a radioactive isotope.

4. A method according to claim 3, wherein the isotope is $^{103}Ru$.

5. A method according to claim 1, wherein said compound covalently binds to said $Ca^{2+}$-binding protein following photo-activation by UV irradiation.

6. A method according to claim 1, wherein said compound binds to the $Ca^{2+}$-binding site of said $Ca^{2+}$-binding protein.

7. A method according to claim 1, wherein said $Ca^{2+}$-binding protein is selected from the group consisting of proteins involved in signal transduction, muscle contraction, neurotransmitter release, hormone secretion, cell motility, apoptosis, fertilization, cell proliferation, cell mitosis and gene expression; proteins associated with $Ca^{2+}$-transport, $Ca^{2+}$-pumps, and with the mitochondrial uniporter; channel protein VDAC; $Ca^{2+}$-release channel/ryanodine receptor; $IP_3$ receptor, proteins involved in $Ca^{2+}$-efflux in mitochondria; and soluble $Ca^{2+}$ binding proteins regulating various cellular activities.

8. A method according to claim 1, wherein said inhibiting treats or mitigates a disorder associated with a defect in the function of said $Ca^{2+}$-binding protein.

9. A method according to claim 1, wherein said AzRu compound, or a solvate thereof, is the active agent in a pharmaceutical composition used in treating a disorder associated with a defect in the function of said $Ca^{2+}$-binding protein.

10. The method of claim 1, wherein the photoreactive azido-ruthenium compound has the empiric formula $Ru_2N_3Cl_5 \cdot 5H_2O$.

\* \* \* \* \*